United States Patent
Hossainy

(10) Patent No.: US 8,007,857 B1
(45) Date of Patent: Aug. 30, 2011

(54) METHODS FOR CONTROLLING THE RELEASE RATE AND IMPROVING THE MECHANICAL PROPERTIES OF A STENT COATING

(75) Inventor: Syed Faiyaz Ahmed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 458 days.

(21) Appl. No.: 11/899,845

(22) Filed: Sep. 7, 2007

Related U.S. Application Data

(60) Provisional application No. 60/843,068, filed on Sep. 8, 2006.

(51) Int. Cl.
*A61L 33/00* (2006.01)

(52) U.S. Cl. ............ 427/2.24; 623/1.15; 623/1.42; 424/423; 427/2.1; 427/2.25

(58) Field of Classification Search ............ 623/1.15, 623/1.42; 424/423; 427/2.24, 2.25
See application file for complete search history.

(56) References Cited

U.S. PATENT DOCUMENTS

| | | | |
|---|---|---|---|
| 5,137,541 A | 8/1992 | Foster | |
| 5,289,831 A | 3/1994 | Bosley | |
| 5,492,763 A | 2/1996 | Barry et al. | |
| 5,837,313 A | 11/1998 | Ding et al. | |
| 6,120,847 A | 9/2000 | Yang et al. | |
| 6,368,658 B1 | 4/2002 | Schwarz et al. | |
| 6,675,595 B2 | 1/2004 | Ohya | |
| 6,676,595 B1 | 1/2004 | Delfino | |
| 6,713,119 B2 | 3/2004 | Hossainy et al. | |
| 6,764,709 B2 | 7/2004 | Flanagan | |
| 7,431,959 B1 | 10/2008 | Dehnad | |
| 7,547,405 B2 * | 6/2009 | Schroeder et al. ............ 264/319 |
| 2003/0082905 A1 | 5/2003 | Hung et al. | |
| 2005/0112172 A1 * | 5/2005 | Pacetti ......................... 424/423 |
| 2005/0171596 A1 * | 8/2005 | Furst et al. ................... 623/1.15 |
| 2008/0317939 A1 | 12/2008 | Dehnad | |

FOREIGN PATENT DOCUMENTS

| WO | WO 00/17889 | * 3/2000 |
|---|---|---|
| WO | WO 03/022323 | 3/2003 |

OTHER PUBLICATIONS

Marmey et al. PVDF multifilament yarns grafted with polystrene induced by gamma radiation: Influence of the grafting parameters on the mechanical properties, 2003, Muclear Instruments and Methods in Physics Research B, vol. 208, pp. 429-433.*

Lu et al., "Phase Separation of SBS Polymer Modified Bitumens", J. of Mat. In Civil Eng. vol. 11, No. 1, pp. 51-57 (1999).

Sipos et al., "Controlled Delivery of Paclitaxel from Stent Coatings Using Poly(hydroxystyrene-*b*-isobutylene-*b*-hydroxystyrene) and Its Acetylated Derivative", Biomacromolecules 6, (5), pp. 2570-2582 (2005).

* cited by examiner

*Primary Examiner* — Dah-Wei D Yuan
*Assistant Examiner* — Andrew Bowman
(74) *Attorney, Agent, or Firm* — Squire, Sanders & Dempsey (US) LLP

(57) ABSTRACT

Methods for controlling the release rate and improving the mechanical properties of a stent coating are disclosed.

3 Claims, No Drawings

METHODS FOR CONTROLLING THE RELEASE RATE AND IMPROVING THE MECHANICAL PROPERTIES OF A STENT COATING

CROSS REFERENCE TO RELATED APPLICATION

This application claims the benefit of and incorporates by reference U.S. Patent Application No. 60/843,068 which was filed on Sep. 8, 2006.

FIELD OF THE INVENTION

The present invention is directed methods for controlling the release rate and improving the mechanical properties of a stent coating.

BACKGROUND OF THE INVENTION

Improving the composition's from which medical articles, such as medical devices and coatings for medical devices, are produced is an ongoing goal of biomaterials research. An example of such a medical device is an implantable medical device.

A stent is an example of an implantable medical device that can benefit from improvements such as, for example, a coating that can be used as a vehicle for delivering pharmaceutically active agents in a predictable manner.

Stents play an important role in a variety of medical procedures such as, for example, percutaneous transluminal coronary angioplasty (PTCA). Stents act as a mechanical intervention to physically hold open and, if desired, expand a passageway within a subject. However, problems with the use of stents can include thrombosis and restenosis, which may develop several months after a particular procedure and create a need for additional angioplasty or a surgical by-pass operation.

To address these problems, stents are being developed to provide for the local delivery of agents, i.e., anti thrombotic and anti restenosis agents. One method of local delivery includes coating the surface of a medical article, e.g., a stent, with a polymeric carrier and attaching an agent to, or blending it with, the polymeric carrier. Agents can be used alone, and in combination. However, there is continual need for novel ways to control the release rate of an agent from a coating and for improving the mechanical properties of a stent coating.

The present invention provides such methods and is also directed to overcoming other deficiencies in the art.

SUMMARY OF THE INVENTION

The present invention relates to a method that involves exposing a stent coated with a drug and polymer to ionizing radiation, wherein the radiation acts to either increase or decrease the degree of cross-linking of the polymer. This method provides a means for controlling the drug release rate and improving the mechanical properties of a coating.

Another aspect of the present invention relates to a method for exposing a stent coated with everolimus and poly(vinylidene-co-hexafluoropropylene) (PVDF-HFP) to either (1) electron beam radiation or (2) gamma radiation under vacuum, wherein the radiation acts to increase the degree of cross-linking of the PVDF-HFP. This method provides a means for controlling the everolimus release rate and improving the mechanical properties of the coating.

A further aspect of the present invention relates to a method that involves exposing a stent coated with paclitaxel and poly(styrene-b-isobutylene-b-styrene) (SIBS) to either (1) electron beam radiation or (2) gamma radiation in the presence of oxygen ($O_2$), wherein the radiation acts to decrease the degree of cross-linking of the SIBS. This method provides a means for controlling the paclitaxel release rate and improving the mechanical properties of the coating.

Another aspect of the present invention relates to a method that involves exposing a stent coated with everolimus and PVDF-HFP to either (1) electron beam radiation or (2) gamma radiation, in the presence of oxygen, then exposing the stent to either (1) electron beam radiation or (2) gamma radiation, under vacuum. This method provides a means for controlling the everolimus release rate and improving the mechanical properties of the coating.

A further aspect of the present invention relates to a method that involves coating a stent with a drug and polymer, wherein during the coating process the stent is exposed to ionizing radiation. This method provides a means for controlling the drug release rate and improving the mechanical properties of the coating.

The present invention provides methods for altering the molecular weight distribution (MWD) of fluoropolymers after drug-eluting stent (DES) coating processes have been completed, or in one situation, during the coating process. These methods act to tailor desired drug release rates as well as stent mechanical properties, and also act to promote favorable biological outcomes such as pro-healing in DES applications.

The present invention takes advantage of the following physical phenomena:
- The MWD of polymers and their state of cross-linking can be altered upon exposure to high energy ionizing radiation, such as electron-beam (e-beam) radiation, gamma radiation and Bremsstrahlung X-ray radiation produced by an accelerator.
- The penetration of X-rays can be as high as one order of magnitude more than the penetration of e-beam radiation.
- The G-factor, i.e., the extent a polymer changes as a result of radiation sterilization, G(X), i.e., the extent of polymer cross-linking, G(S), i.e., the extent of polymer chain scission, and G(Gas), i.e., the extent of gaseous product of the polymer post-sterilization, depends on the type of polymer and the dose of ionizing radiation.
- $G(X)<G(S)$ in the presence of $O_2$, in contrast to under vacuum.
- At low ionizing radiation dosages, i.e., less than 20 Mrad, polyvinylidene fluoride (PVDF), poly(tetrafluoroethylene) (PTFE) and ultra high molecular weight polyethylene (UHMPE) increase in crystallinity while at high doses, i.e., around 2000 Mrad, both the degree of crystallinity and the Tm drops, e.g., the Tm drops by around 25° C. for poly(ethylene terephthalate) (PET).
- The presence of an aromatic group, e.g., on polystyrene, has a protective effect on both G(S) and G(X).

The present invention takes advantage of the above physical phenomena to design improved stent coatings using fluoropolymers, poly(styrene-b-isobutylene-b-styrene) (SIBS), and styrene-butadiene-styrene (SBS) polymers in conjunction with everolimus, paclitaxel and sirolimus as specific drugs, several embodiments of which are presented below.

In a first embodiment, a poly(vinylidene-co-hexafluoropropylene) (PVDF-HFP)+everolimus-coated stent will be e-beam sterilized in a vacuum. This will enhance the degree of cross-linking of the PVDF-HFP polymer and improve its mechanical properties upon deployment in vivo.

In a second embodiment, a SIBS+paclitaxel-coated stent will be e-beam sterilized in the presence of $O_2$ at 0° C. This will reduce the G(X) for the system, i.e., decrease the degree of cross-linking of the SIBS.

In a third embodiment, a PVDF-HFP+everolimus-coated stent will first be e-beam sterilized in $O_2$, then in a vacuum. The resultant polymer will have different structural properties than PVDF-HFP, thereby altering the drug release rate and improving the mechanical properties of the coating.

In a fourth embodiment, gamma irradiation will be used in place of e-beam radiation for each of the first three embodiments of the present invention.

In a fifth embodiment, instead of applying ionizing radiation, i.e., e-beam or gamma radiation, to a DES after the coating process has been completed, the radiation can be applied during the coating process. This will be achieved by sequential coating and exposure to ionizing radiation. Employing this strategy will enable more changes in the bulk of the polymer coating; however, the final objectives achieved will be similar to the post-coating embodiments set forth above.

DETAILED DESCRIPTION

The present invention relates to a method that involves exposing a stent coated with a drug and polymer to ionizing radiation, wherein the radiation acts to either increase or decrease the degree of cross-linking of the polymer. This method provides a means for controlling the drug release rate and improving the mechanical properties of a coating.

Another aspect of the present invention relates to a method for exposing a stent coated with everolimus and PVDF-HFP to either (1) electron beam radiation or (2) gamma radiation under vacuum, wherein the radiation acts to increase the degree of cross-linking of the PVDF-HFP. This method provides a means for controlling the everolimus release rate and improving the mechanical properties of the coating.

A further aspect of the present invention relates to a method that involves exposing a stent coated with paclitaxel and SIBS to either (1) electron beam radiation or (2) gamma radiation in the presence of oxygen ($O_2$), wherein the radiation acts to decrease the degree of cross-linking of the SIBS. This method provides a means for controlling the paclitaxel release rate and improving the mechanical properties of the coating. Another aspect of the present invention relates to a method that involves exposing a stent coated with everolimus and PVDF-HFP to either (1) electron beam radiation or (2) gamma radiation, in the presence of oxygen, then exposing the stent to either (1) electron beam radiation or (2) gamma radiation, under vacuum. This method provides a means for controlling the everolimus release rate and improving the mechanical properties of the coating.

A further aspect of the present invention relates to a method that involves coating a stent with a drug and polymer, wherein during the coating process the stent is exposed to ionizing radiation. This method provides a means for controlling the drug release rate and improving the mechanical properties of the coating.

According to the present invention, a stent coated with a drug and polymer will be exposed to ionizing radiation to provide a means for controlling the drug release rate and improving the mechanical properties of a stent coating, as well as promote favorable biological outcomes such as pro-healing in DES applications.

According to the present invention, a stent is a medical substrate that can be implanted in a human or veterinary patient. Examples of stents include self-expandable stents and balloon-expandable stents. The underlying structure of the stent can be of virtually any design. The stent can be made of a metallic material or an alloy.

Suitable methods for coating a stent with a drug and polymer are known to those skilled in the art. Suitable drugs are known to those skilled in the art, but preferably include everolimus, paclitaxel and sirolimus. Suitable polymers are known to those skilled in the art, but preferably include fluoropolymers, PVDF-HFP, SIBS and SBS.

According to the present invention, suitable sources of ionizing radiation include electron beam radiation, gamma radiation and Bremsstrahlung X-ray radiation.

The present invention provides several means for controlling the drug release rate and improving the mechanical properties of a stent coating. Each method involves exposing a drug/polymer-coated stent to ionizing radiation, either in the presence of oxygen or under vacuum. This ionizing radiation exposure acts to either increase or decrease the degree of cross-linking of the polymer present in the coating, thereby providing a means for controlling the release rate and improving the mechanical properties of the stent coating. Five mechanisms for achieving this, as encompassed by the present invention, are described above in accordance with the present invention.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

The invention claimed is:

1. A method comprising:
   exposing a stent coated with everolimus and poly(vinylidene-co-hexafluoropropylene) first to either (1) electron beam radiation in the presence of oxygen or (2) gamma radiation in the presence of oxygen;
   and second, exposing the stent coated with everolimus and poly(vinylidene-co-hexafluoropropylene) to either (1) electron beam radiation under vacuum or (2) gamma radiation under vacuum;
   thereby providing a means for controlling the everolimus release rate and improving the mechanical properties of the coating.

2. The method of claim 1, wherein the first exposure and the second exposure are to electron beam radiation.

3. The method of claim 1, wherein the first exposure and the second exposure are to gamma radiation.

* * * * *